United States Patent
Tabandeh et al.

(10) Patent No.: US 11,625,107 B2
(45) Date of Patent: Apr. 11, 2023

(54) SYSTEM AND METHOD FOR MOTION MODE MANAGEMENT

(71) Applicant: INTUITIVE SURGICAL OPERATIONS, INC., Sunnyvale, CA (US)

(72) Inventors: Saleh Tabandeh, Santa Clara, CA (US); Caroline A. Edwards, San Francisco, CA (US); Angel Jeremy Perez Rosillo, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 399 days.

(21) Appl. No.: 16/914,165

(22) Filed: Jun. 26, 2020

(65) Prior Publication Data
US 2020/0409477 A1 Dec. 31, 2020

Related U.S. Application Data

(60) Provisional application No. 62/867,624, filed on Jun. 27, 2019.

(51) Int. Cl.
*B25J 9/16* (2006.01)
*B25J 13/02* (2006.01)
(Continued)

(52) U.S. Cl.
CPC ............ *G06F 3/0346* (2013.01); *A61B 34/37* (2016.02); *B25J 9/1682* (2013.01); *B25J 9/1689* (2013.01); *B25J 13/025* (2013.01)

(58) Field of Classification Search
CPC ...... A61B 2034/2059; A61B 2090/064; A61B 2090/066; A61B 2090/306;
(Continued)

(56) References Cited

U.S. PATENT DOCUMENTS

| 7,107,124 B2 * | 9/2006 | Green | A61B 34/72 700/262 |
| 8,246,608 B2 * | 8/2012 | Omori | A61B 34/70 606/1 |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Jaime Figueroa
(74) *Attorney, Agent, or Firm* — Artegis Law Group, LLP

(57) ABSTRACT

Systems and methods for motion mode management include a computer-assisted device having an input control, a repositionable structure, and a controller coupled to the input control and the repositionable structure. The controller is configured to detect movement of the input control, control movement of the repositionable structure based on the movement of the input control, determine whether the movement of the input control is likely to include one or more components of a mode switching movement of the input control, and in response to determining that the movement of the input control is likely to include one or more components of the mode switching movement, temporarily disable mode switching in response to movement of the input control. The mode switching movement changes a mode of operation for the device. In some embodiments, the temporarily disabling prevents changing the mode of operation when the movement is a mode switching movement.

24 Claims, 4 Drawing Sheets

(51) Int. Cl.
*G06F 3/0346* (2013.01)
*A61B 34/37* (2016.01)

(58) Field of Classification Search
CPC ........ A61B 2090/371; A61B 2090/376; A61B 2090/378; A61B 34/37; A61B 34/76; A61B 2034/2048; G06F 3/0346; B25J 9/1682; B25J 9/1689; B25J 13/025
USPC .................................. 606/19; 700/245–264; 318/568.11–568.25
See application file for complete search history.

(56) References Cited

U.S. PATENT DOCUMENTS

| | | | |
|---|---|---|---|
| 8,620,473 B2 | 12/2013 | Diolaiti et al. | |
| 8,903,546 B2 | 12/2014 | Diolaiti et al. | |
| 8,918,211 B2 | 12/2014 | Diolaiti et al. | |
| 9,084,623 B2 | 7/2015 | Gomez et al. | |
| 9,138,129 B2 | 9/2015 | Diolaiti | |
| 9,173,548 B2 * | 11/2015 | Omori | A61B 34/30 |
| 9,241,767 B2 * | 1/2016 | Prisco | B25J 9/1674 |
| 9,333,042 B2 | 5/2016 | Diolaiti et al. | |
| 9,439,668 B2 * | 9/2016 | Timm | H01H 23/28 |
| 9,469,034 B2 | 10/2016 | Diolaiti et al. | |
| 9,492,927 B2 * | 11/2016 | Diolaiti | A61B 34/30 |
| 9,586,323 B2 | 3/2017 | Diolaiti et al. | |
| 9,622,826 B2 | 4/2017 | Diolaiti et al. | |
| 9,629,520 B2 | 4/2017 | Diolaiti | |
| 9,956,044 B2 | 5/2018 | Gomez et al. | |
| 10,188,472 B2 | 1/2019 | Diolaiti et al. | |
| 10,271,915 B2 * | 4/2019 | Diolaiti | A61B 90/30 |
| 10,561,469 B2 * | 2/2020 | Kasai | A61B 34/32 |
| 10,835,336 B2 * | 11/2020 | Vokrot | A61B 34/74 |
| 2005/0065658 A1 * | 3/2005 | Green | A61B 17/00234 348/E13.016 |
| 2007/0142825 A1 * | 6/2007 | Prisco | A61B 34/70 606/1 |
| 2009/0062814 A1 * | 3/2009 | Omori | A61B 34/71 606/130 |
| 2010/0262162 A1 * | 10/2010 | Omori | A61B 34/70 606/130 |
| 2011/0282359 A1 * | 11/2011 | Duval | A61M 13/003 606/130 |
| 2012/0059391 A1 * | 3/2012 | Diolaiti | A61B 34/30 606/130 |
| 2013/0267975 A1 * | 10/2013 | Timm | H01H 23/28 606/169 |
| 2013/0282003 A1 * | 10/2013 | Messerly | A61B 18/1442 606/169 |
| 2013/0310639 A1 * | 11/2013 | Omori | A61B 34/71 600/102 |
| 2016/0374767 A1 | 12/2016 | Diolaiti et al. | |
| 2017/0007342 A1 * | 1/2017 | Kasai | A61B 34/30 |
| 2017/0035521 A1 * | 2/2017 | Diolaiti | A61B 34/77 |
| 2017/0086933 A1 * | 3/2017 | Ogawa | A61B 34/74 |
| 2017/0129108 A1 | 5/2017 | Diolaiti et al. | |
| 2017/0156806 A1 * | 6/2017 | Prisco | B25J 9/1674 |
| 2017/0173788 A1 | 6/2017 | Diolaiti et al. | |
| 2018/0193102 A1 * | 7/2018 | Inoue | A61B 1/05 |
| 2018/0296291 A1 * | 10/2018 | Vokrot | B25J 13/025 |
| 2019/0125459 A1 * | 5/2019 | Shelton, IV | A61B 90/30 |
| 2019/0201043 A1 * | 7/2019 | Shelton, IV | A61B 17/320092 |
| 2019/0328479 A1 * | 10/2019 | Wada | G02B 21/0012 |
| 2019/0328481 A1 * | 10/2019 | Kamikawa | A61B 90/20 |
| 2020/0289229 A1 * | 9/2020 | Denlinger | A61B 1/04 |
| 2022/0183697 A1 * | 6/2022 | Tanaka | A61B 17/1285 |

* cited by examiner

SYSTEM AND METHOD FOR MOTION MODE MANAGEMENT

RELATED APPLICATIONS

This application claims priority benefit of the U.S. Provisional Patent Application No. 62/867,624, filed Jun. 27, 2019, which is incorporated by reference herein.

TECHNICAL FIELD

The present disclosure relates generally to operation of devices having instruments with end effectors mounted to manipulators and more particularly to operation of the devices to manage the modes by which instruments are manipulated by input controls.

BACKGROUND

More and more devices are being replaced with computer-assisted electronic devices. This is especially true in industrial, entertainment, educational, and other settings. As a medical example, the hospitals of today with large arrays of electronic devices being found in operating rooms, interventional suites, intensive care wards, emergency rooms, and/or the like. For example, glass and mercury thermometers are being replaced with electronic thermometers, intravenous drip lines now include electronic monitors and flow regulators, and traditional hand-held surgical and other medical instruments are being replaced by computer-assisted medical devices.

These computer-assisted devices are useful for performing operations and/or procedures on materials, such as the tissue of a patient, that are located in a workspace. When the workspace is separated from the operator controlling the computer-assisted device, it is common for the operator to control the computer-assisted device using teleoperation and to monitor the activity of the computer-assisted device using an imaging device positioned to capture images or video of the workspace. In computer-assisted devices with instruments that are mounted to repositionable arms and/or manipulators, the teleoperation typically involves the operator using one or more input controls to provide movement commands for the instruments that are, for example, implemented by driving one or more joints in a respective repositionable arm and/or manipulator. In some computer-assisted devices, the imaging device may also be mounted to its own repositionable arm and/or manipulator so that the operator may change a location and/or a direction of a field of view of the imaging device so as to be able to capture images of the workspace from different positions and orientations.

Different instruments may be teleoperated in different ways and some instruments may be teleoperated in one of two or more possible movement modes. Examples of possible movement modes include an independent movement mode where an instrument is operated independently of other instruments, a dependent movement mode where the instrument is operated based on the movement of other instruments, and/or the like. To switch between the different movement modes, the operator typically performs an action that indicates that a mode switch should occur. In some examples, the action may include activation of an input device, performing an action on a graphical user interface (GUI), and/or the like.

Accordingly, it would be advantageous to have methods and systems to manage the modes by which instruments are manipulated by input controls.

SUMMARY

Consistent with some embodiments, a computer-assisted device includes an input control, a repositionable structure, and a controller coupled to the input control and the repositionable structure. The controller is configured to detect movement of the input control, control movement of the repositionable structure based on the movement of the input control, determine whether the movement of the input control is likely to include one or more components of a mode switching movement of the input control, and in response to determining that the movement of the input control is likely to include one or more components of the mode switching movement, temporarily disable mode switching in response to movement of the input control. The mode switching movement changes a mode of operation for the computer-assisted device.

Consistent with some embodiments, a method of operating a computer-assisted device include detecting, by a controller, movement of an input control of the computer-assisted device; controlling, by the controller, movement of a repositionable structure of the computer-assisted device based on the movement of the input control; determining, by the controller, whether the movement of the input control is likely to include one or more components of a mode switching movement of the input control; and in response to determining that the movement of the input control is likely to include one or more components of the mode switching movement, temporarily disabling, by the controller, mode switching in response to movement of the input control. The mode switching movement changes a mode of operation for the computer-assisted device.

Consistent with some embodiments, a non-transitory machine-readable medium including a plurality of machine-readable instructions which when executed by one or more processors are adapted to cause the one or more processors to perform any of the methods described herein.

Figure 1:
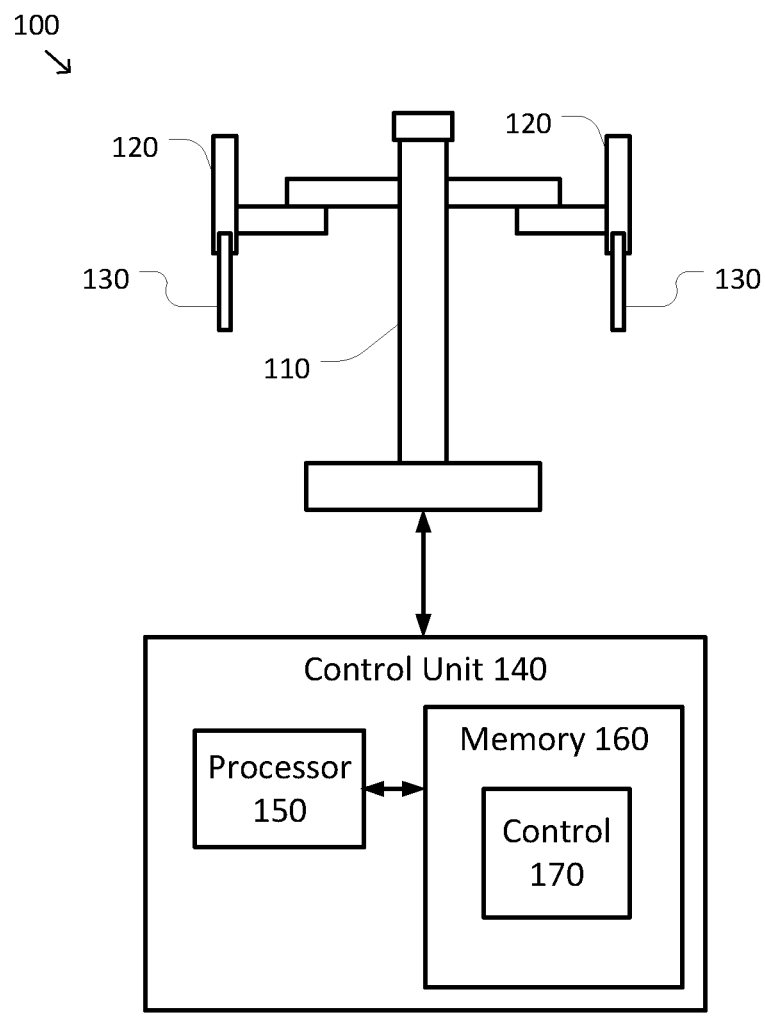
FIG. 1 is a simplified diagram of a computer-assisted system according to some embodiments.

In the figures, elements having the same designations have the same or similar functions.

DETAILED DESCRIPTION

This description and the accompanying drawings that illustrate inventive aspects, embodiments, implementations, or modules should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

In this description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Further, this description's terminology is not intended to limit the invention. For example, spatially relative terms-such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the elements or their operation in addition to the position and orientation shown in the figures. For example, if the content of one of the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes include various special element positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements described in detail with reference to one embodiment, implementation, or module may, whenever practical, be included in other embodiments, implementations, or modules in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

In some instances, well known methods, procedures, components, and circuits have not been described in detail so as not to unnecessarily obscure aspects of the embodiments.

This disclosure describes various devices, elements, and portions of computer-assisted devices and elements in terms of their state in three-dimensional space. As used herein, the term "position" refers to the location of an element or a portion of an element in a three-dimensional space (e.g., three degrees of translational freedom along Cartesian x-, y-, and z-coordinates). As used herein, the term "orientation" refers to the rotational placement of an element or a portion of an element (three degrees of rotational freedom—e.g., roll, pitch, and yaw). As used herein, the term "shape" refers to a set positions or orientations measured along an element. As used herein, and for a device with repositionable arms, the term "proximal" refers to a direction toward the base of the computer-assisted device along its kinematic chain and "distal" refers to a direction away from the base along the kinematic chain.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, Calif. Knowledgeable persons will understand, however, that inventive aspects disclosed herein may be embodied and implemented in various ways, including robotic and, if applicable, non-robotic embodiments and implementations. Implementations on da Vinci® Surgical Systems are merely exemplary and are not to be considered as limiting the scope of the inventive aspects disclosed herein. For example, techniques described with reference to surgical instruments and surgical methods may be used in other contexts. Thus, the instruments, systems, and methods described herein may be used for humans, animals, portions of human or animal anatomy, industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

FIG. 1 is a simplified diagram of a computer-assisted system 100 according to some embodiments. As shown in FIG. 1, computer-assisted system 100 includes a computer-assisted device 110 with a repositionable structure having one or more repositionable arms 120. Each of the one or more repositionable arms 120 may support one or more instruments 130. In some examples, computer-assisted device 110 may be consistent with a computer-assisted medical device. The one or more instruments 130 may include non-imaging instruments, imaging devices, and/or the like. In some medical examples, the instruments may include medical instruments, such as clamps, grippers, retractors, cautery instruments, suction instruments, suturing devices, and/or the like. In some medical examples, the imaging devices may include endoscopes, cameras, ultrasonic devices, fluoroscopic devices, and/or the like. In some examples, each of the one or more instruments 130 may be inserted into a workspace (e.g., anatomy of a patient, a veterinary subject, and/or the like) through a respective cannula docked to a respective one of the one or more repositionable arms 120. In some examples, a direction of a field of view of an imaging device may correspond to an insertion axis of the imaging device and/or may be at an angle relative to the insertion axis of the imaging device. In some examples, each of the one or more instruments 130 may include an end effector that may be capable of both grasping a material (e.g., tissue of a patient) located in the workspace and delivering energy to the grasped material. In some examples, the energy may include ultrasonic, radio frequency, electrical, magnetic, thermal, light, and/or the like. In some embodiments, computer-assisted system 100 may be found in an operating room and/or an interventional suite. In some examples, each of the one or more repositionable arms 120 and/or the one or more instruments 130 may include one or more joints.

Computer-assisted device 110 is coupled to a control unit 140 via an interface. The interface may include one or more cables, connectors, and/or buses and may further include one or more networks with one or more network switching and/or routing devices. Control unit 140 includes a processor 150 coupled to memory 160. Operation of control unit 140 is controlled by processor 150. And although control unit 140 is shown with only one processor 150, it is understood that processor 150 may be representative of one or more central processing units, multi-core processors, microprocessors, microcontrollers, digital signal processors, field programmable gate arrays (FPGAs), application specific integrated circuits (ASICs), graphics processing units (GPUs), tensor processing units (TPUs), and/or the like in control unit 140. Control unit 140 may be implemented as a stand-alone subsystem and/or as a board added to a computing device or as a virtual machine.

Memory 160 may be used to store software executed by control unit 140 and/or one or more data structures used during operation of control unit 140. Memory 160 may include one or more types of machine-readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 160 includes a control module 170 that is responsible for controlling one or more aspects of the operation of computer-assisted device 110 including, for example, the control of movement and/or operation of each of the one or more repositionable arms 120, the control of movement and/or operation of each of the one or more instruments 130, the management of modes of operation of computer-assisted device 110, and/or the like as is described in further detail below. And although control module 170 is characterized as a software module, control module 170 may be implemented using software, hardware, and/or a combination of hardware and software.

As discussed above and further emphasized here, FIG. 1 is merely an example which should not unduly limit the scope of the claims. One of ordinary skill in the art would recognize many variations, alternatives, and modifications. According to some embodiments, computer-assisted system 100 may include any number of computer-assisted devices with articulated arms and/or instruments of similar and/or different in design from computer-assisted device 110. In some examples, each of the computer-assisted devices may include fewer or more articulated arms and/or instruments.

Figure 2:
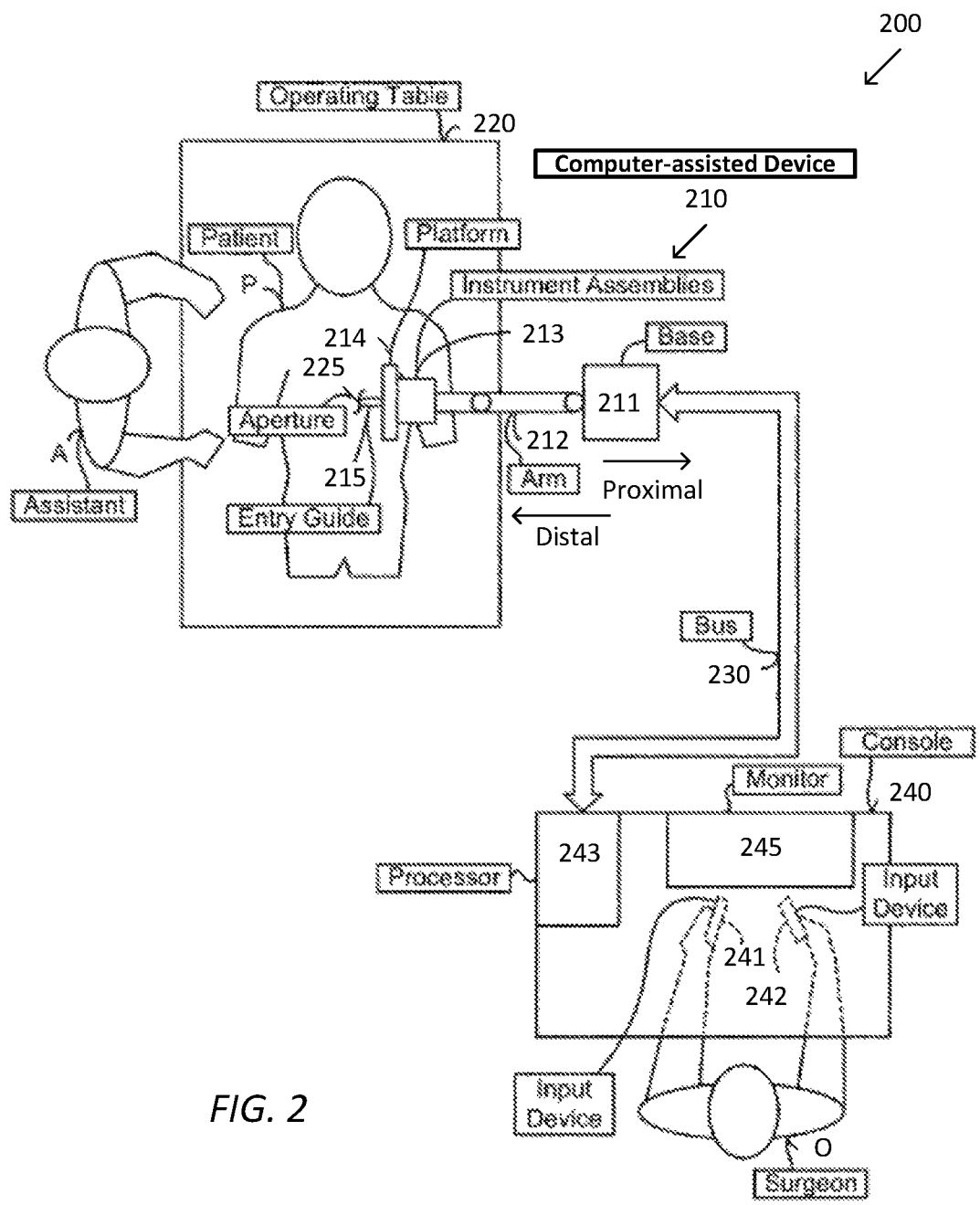
FIG. 2 is a simplified diagram of a computer-assisted device according to some medical embodiments.

FIG. 2 is a simplified diagram of a computer-assisted system 200 according to some medical embodiments. In some embodiments, computer-assisted system 200 may be consistent with computer-assisted system 100. As shown in FIG. 2, computer-assisted system 200 includes a computer-assisted device 210, which may be consistent with computer-assisted device 110. Computer-assisted device 210 includes a base 211 located at a proximal end of a kinematic chain for computer-assisted device 210. During a procedure, computer-assisted device 210 and base 211 may be positioned adjacent to a workspace, such as a patient P as shown in FIG. 2. A repositionable arm 212 is coupled to base 211. In some examples, repositionable arm 212 may include one or more joints for changing a position and/or an orientation of a distal end of repositionable arm 212 relative to base 211. A set of instrument assemblies 213 is mounted toward the distal end of repositionable arm 212. Each of the instrument assemblies 213 may be used to control a respective instrument (not shown). The instrument assemblies 213 are attached to a platform 214, which supports an entry guide 215 through which the instruments are passed to gain access to a worksite. The worksite corresponds to the interior anatomy of patient P in the examples of FIG. 2. Patient P is located on a surgical table 220 and the access to the interior anatomy of patient P is obtained through an aperture 225, such as an incision site on patient P and/or a natural body orifice of patient P. In some examples, access through the aperture 225 may be made through a port, a cannula, a trocar, and/or the like. In some examples, the worksite may correspond to exterior anatomy of patient P, or a non-patient related worksite.

Also shown in FIG. 2 is an operator console 240 coupled to computer-assisted device 210 through a bus 230. In some examples, bus 230 may be consistent with the interface between control unit 140 and computer-assisted device 110 in FIG. 1. Operator console 240 includes two input devices 241 and 242, which may be manipulated by an operator O (e.g., a surgeon as shown) to control movement of computer-assisted device 210, repositionable arm 212, instrument assemblies 213, the instruments, and/or the like through, for example, teleoperational control. Operator console 240 further includes a processor 243, which may be consistent with control unit 140 and/or processor 150. To aid operator O in the control of computer-assisted device 210, operator console 240 further includes a monitor 245, which is configured to display images and/or video of the worksite captured by an imaging device. In some examples, monitor 245 may be a stereoscopic viewer. In some examples, the imaging device may be one of the instruments of the computer-assisted device 210, such as an endoscope, a stereoscopic endoscope, and/or the like. Operator O and/or computer-assisted device 210 may also be supported by a patient-side assistant A.

Figure 3:
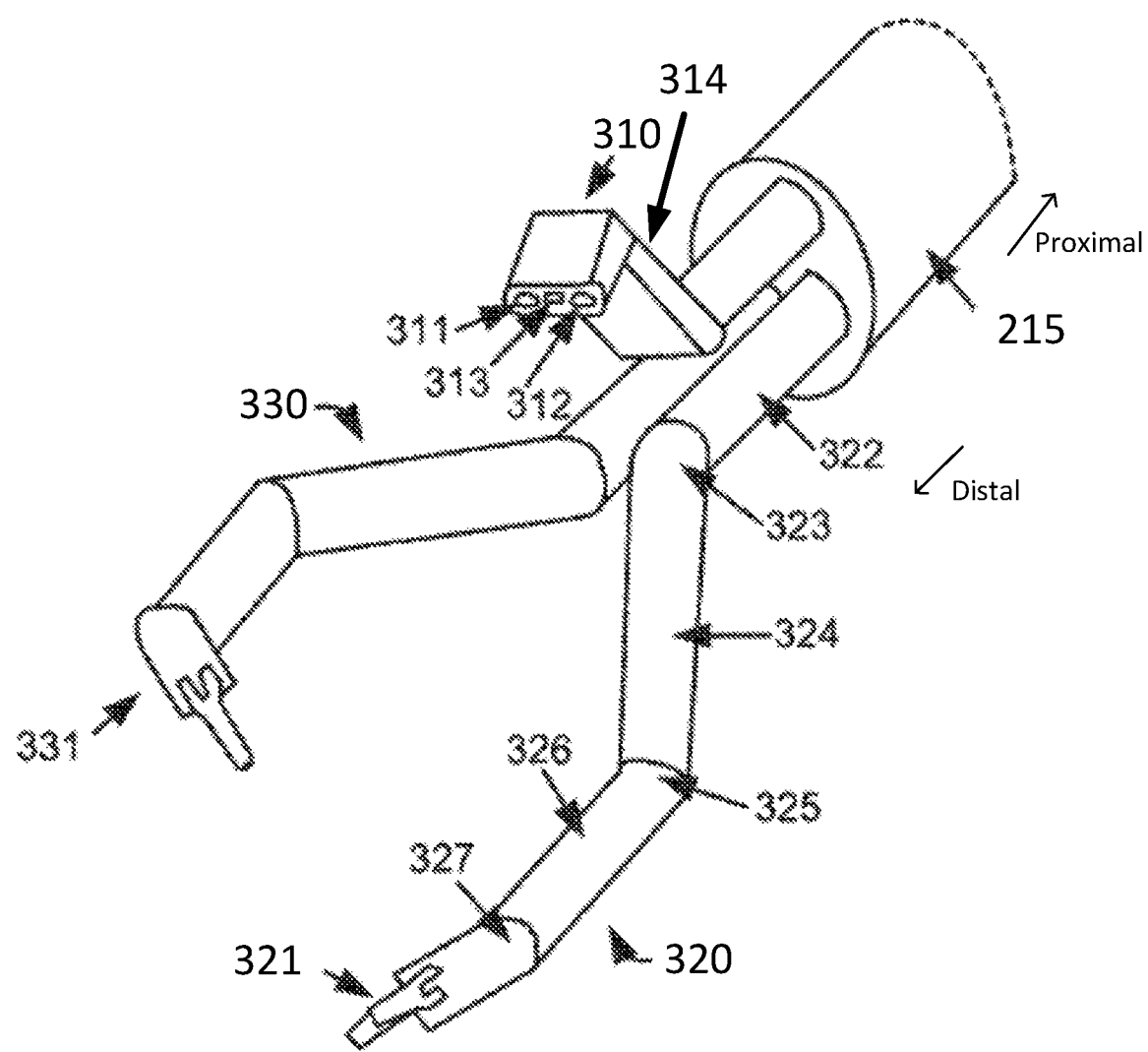
FIG. 3 is a simplified diagram of a distal end of a computer-assisted device having an imaging device and multiple instruments according to some medical embodiments.

FIG. 3 is a simplified diagram of a distal end of a computer-assisted device having an imaging device and multiple instruments according to some medical embodiments. In some embodiments, the computer-assisted device may be consistent with computer-assisted device 110 and/or 210. As shown in FIG. 3, the distal end of the computer-assisted device includes entry guide 215 through which an instrument 310 comprising an imaging device (also referred to as "imaging device 310") and two additional instruments 320 and 330 may be inserted to, or otherwise placed at, a worksite. In the examples of FIG. 3, imaging device 310 utilizes optical technology and includes a pair of stereoscopic image capturing elements 311 and 312 and an illumination source 313 for illuminating the worksite. In some examples, the illumination source 313 may be located in a distal portion of imaging device 310 and/or may be located proximal to imaging device 310 with the illumination guided to the distal end via a fiber optic cable. In some examples, imaging device 310 utilizes other imaging modalities that may or may not require an illumination source, such as ultrasonic imaging and/or the like. Imaging device 310 further includes an articulable structure 314, which may include one or more joints and links for changing a position and/or an orientation of the distal portion of imaging device 310 relative to entry guide 215. In some examples, the imaging device 310 may be coupled to a repositionable arm of a repositionable structure (e.g. repositionable arm 120); when thus coupled, articulable structure 314 can form part of that repositionable structure.

Instruments 320 and 330 also include respective articulable structures with respective end effectors 321 and 331 located at their respective distal portions. As a representative example, the articulable structure of instrument 320 is shown with various joints and links 322-327. Like imaging device 310, the distal portions of instruments 320 and 330 (e.g., end effectors 321 and 331, respectively) may have their positions and/or orientations relative to entry guide 215 changed through manipulation of the articulable structures.

The examples of computer-assisted devices 110 and/or 210 in FIGS. 1-3 illustrate that the links and joints used to control the positions and/or orientations of the distal portions of the instruments 130, 310, 320, and/or 330 may be classified into two types of links and joints. The first type of links and joints are shared (sometimes referred to as common mode) links and joints. Shared links and joints have the characteristic that manipulation of the shared links and joints (e.g., by articulating the shared joints with respective actuators) repositions by translating and/or reorienting two or more of the instruments and/or the distal portions of the instruments as a combined unit. This is because the shared links and joints are coupled in series with the kinematic chains specific to the two or more instruments, and the shared links and joints are located proximal to the two or more instruments. Examples of shared links and joints from FIGS. 1-3 include the links and joints in a base and vertical column of computer-assisted device 110, the links and joints of base 211, and/or the links and joints of repositionable arm 212.

The second type of links and joints are independent (sometimes referred to as differential mode) links and joints. Independent links and joints have the characteristic that manipulation of the independent links and joints (e.g., by articulating the independent joints with respective actuators) repositions by translating and/or reorienting only the instrument and/or the distal portion of the instrument with which they are associated. This is because the independent links and joints are located on only the kinematic chain of their respective instrument. Examples of independent links and joints from FIGS. 1-3 include the links and joints in repositionable arms 120, the links and joints in instruments 130, the links and joints of articulable structure 314 of imaging device 310, and/or the links and joints of the articulable structures of instruments 320 and/or 330.

Although the computer-assisted devices 110 and/or 210 in FIGS. 1-3 illustrate particular devices comprising both shared and independent links and joints, in some embodiments, computer-assisted devices may comprise other physical architectures. For example, computer-assisted devices may comprise only independent links and joints, and no shared links and joints.

During a procedure with a computer-assisted device, an operator (e.g., operator O) may find it advantageous to control the instruments (e.g., instruments 130, 310, 320, and/or 330) and/or end effectors according to different operating modes. In some examples, one of the operating modes may include moving one of the instruments independently according to corresponding motion of an input control (e.g., one of input devices 241 and/or 242) such as by, for example, having movement of the instrument following movement of the input control. In some examples, another of the operating modes may include moving one of the instruments independently according to combined motion of two input controls such as by, for example, modeling the two input controls as if they correspond to two ends of a handlebar connected via a rigid link and "steering" the movement of the instrument using the "handlebar" represented by the two input controls. In some examples, others of the operating modes may include moving two or more instruments together (e.g., by maintaining a same relative position and/or orientation between the two or more instruments such as by, for example, using an input control or two input controls as a "handlebar" and moving the two or more instruments together using their shared links and joints (one mode), using their independent links and joints in cooperative fashion (another mode), and/or using both their shared and independent links and joint (yet another mode). In some examples, others of the operating modes may include a mode where one or more other instruments are moved to maintain a same position and/or orientation to an imaging device (e.g., imaging device 310) that is being moved and/or in another mode where the one or more other instruments are kept stationary in a workspace while the imaging device is being moved.

To support two or more modes, the computer-assisted device includes one or more mechanisms for determining when a switch in modes should occur, and for switching the mode in accordance with the determination. In some examples, the operator may perform an action to indicate that the operator would like to switch from a current mode to a different mode. In some examples, the operator may activate and/or operate one or more input devices used to indicate the desired mode of operation. In some examples, the one or more input devices may include one or more buttons, switches, levers, pedals, dials, and/or the like. Examples of systems using input devices such as buttons, switches, levers, pedals, dials, and/or the like to select an operating mode are described in further detail in commonly owned U.S. Pat. No. 9,586,323 disclosing "User Selection of Robotic System Operating Modes Using Mode Distinguishing Operator Actions," which is incorporated by reference herein. In some examples, the operator may activate one or more elements on a GUI (e.g., a button, a menu, a slider, a widget, and/or the like) to indicate the desired mode of operation. In some examples, the operator may issue a voice command, perform a hand gesture, and/or the like to indicate the desired mode.

According to some embodiments, the computer-assisted device may include one or more input controls (e.g., input devices 241 and/or 242) used to specify the motion of one or more instruments, such as through teleoperation. In some examples, in order to reduce the number of input controls that are needed to indicate the modes of operation (e.g., to reduce the number of buttons, switches, levers, pedals, dials, and/or the like) certain movement of the one or more of the input controls (e.g., mode switch movement) used to specify the motion of the one or more instruments may be used to specify a desired switch in mode rather than a desired motion of the one or more instruments (e.g., the functionality of these input controls is overloaded). In some examples, the mode switch movement may include movement that is less likely to be used when controlling the desired location of the one or more instruments. In some examples, the mode switch movement may include a quick rotation of an input control in a first direction about an axis near a centroid of the input control followed by a quick rotation of the input control in a second direction, opposite the first direct, about the same or approximately the same axis. In some examples, the mode switch movement may include a quick movement of the input control in a first direction followed by a quick movement of the input control in a direction approximately opposite the first direction (e.g., up-down, down-up, left-right, right-left, in-out, out-in, and/or the like), a quick zig-zag motion, and/or the like.

However, once an input control is used to specify a desired motion for one or more instruments and to specify a desired mode switch, it is possible that the movement used to specify the desired motion may be inadvertently confused for movement used to specify a desired mode switch with the result that an unintended switch in mode occurs. Accordingly, it would be advantageous to detect when movement of one or more input controls that are being used to specify desired motion of one or more instruments is likely to be confused for a desired mode switch, and, in response, temporarily disable the detection of mode switch movement. Thus, in effect, preventing a switch between modes even though the movement of the one or more input controls is a mode switch movement.

Figure 4:
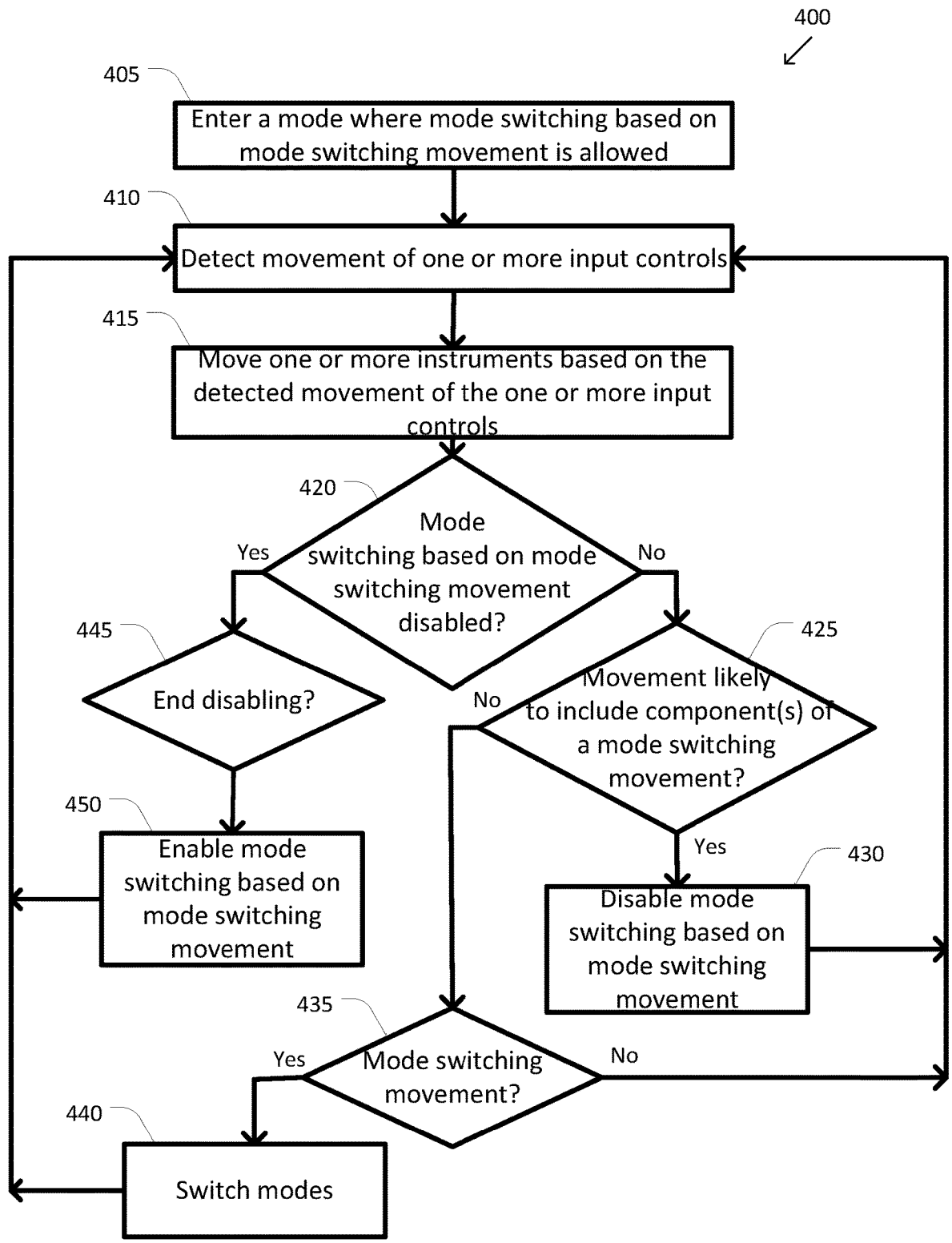
FIG. 4 is a simplified diagram of a method of managing modes according to some embodiments.

FIG. 4 is a simplified diagram of a method 400 of managing modes according to some embodiments. One or more of the processes 405-450 of method 400 may be implemented, at least in part, in the form of executable code stored on non-transitory, tangible, machine readable media that when run by one or more processors (e.g., the processor 150 in control unit 140 and/or processor 243) may cause the one or more processors to perform one or more of the processes 405-450. In some embodiments, method 400 may be performed by one or more modules, such as control module 170. In some embodiments, method 400 may be used to monitor movement in one or more input controls (e.g., input device 241 and/or 242), use the movement to move one or more instruments (e.g., instrument 130, 310, 320, and/or 330), detect when the movement is likely to include one or more components of a mode switch movement, and temporarily disable mode switching based on movement of the one or more input controls.

At a process 405, a mode is entered where mode switching based on mode switching movement is allowed. In some examples, the mode may include any mode where movement of one or more input controls (e.g., input device 241 and/or 242) are used to control movement of one or more instruments (e.g., instrument 130, 310, 320, and/or 330), such as by using teleoperation. In some examples, the mode may include any of the modes described above. In some examples, the mode may be a mode where one or more instruments are controlled independently and/or in a coordinated fashion. In some examples, the mode may be a mode where the one or more instruments are controlled using one input control, using two input controls (e.g., a "handlebar" mode), and/or the like. In some examples, process 405 may further include enabling the detection of mode switching movement.

At a process 410, movement of the one or more input controls is detected. In some examples, the detected movement may include a translation of one or more of the one or more input controls, a rotation of one or more of the one or more input controls, and/or both a translation and a rotation of one or more of the one or more input controls. In some examples, the detected movement may include information associated with both a position of each of the one or more input controls, a velocity (linear and/or rotational) of each of the one or more input controls, an acceleration (linear and/or rotational) of each of the one or more input controls, and/or the like and/or any combination thereof. In some examples, the movement may include a tracked position, velocity, acceleration, and/or the like of the one or more input controls over a period of time so that movement over time may be monitored to detect one or more patterns of movement of the one or more input controls. In some examples, the movement may be detected using one or more sensors (e.g., encoders, and/or the like) associated with each of the joints in the kinematic chains of the one or more input controls, inertial management units, tracking units, imaging systems, and/or the like.

At a process 415, the one or more instruments are moved based on the detected movement of the one or more input controls. In some examples, the way the one or more instruments are moved may depend on the mode, such as the mode entered during process 405 and/or the mode switched to during process 440 as is described in further detail below. Depending on the mode, the one or more instruments may be moved independently and/or in a coordinated fashion. Depending on the mode, each of the one or more instruments may be moved based on movement of one of the one or more input controls, based on movement of two input controls (e.g., a "handlebar" mode), and/or the like. In some examples, the one or more instruments may be moved by sending one or more currents, voltages, pulse-width modulated signals and/or the like to one or more actuators and/or controllers used to move the joints in the kinematic chains of the one or more instruments.

At a process 420, it is determined whether mode switching based on mode switching movement is disabled. Before the movement detected during process 410 is examined to determine whether it indicates that a switch in mode should occur, it is determined whether mode switching based on mode switching movement is disabled (e.g., by process 430 as is described in further detail below). When it is determined that mode switching based on mode switching movement is not disabled, the movement is further analyzed beginning with a process 425. When it is determined that mode switching based on mode switching movement is disabled, processing continues with a process 445.

At the process 425, it is determined whether the movement is likely to include one or more components of a mode switching movement. In many situations it is possible that movement of the one or more input controls made to move the one or more instruments may include one or more components that include one or more components that may be similar to one or more components of a movement used to indicate a switch in mode. As a non-limiting example, a rotational motion of one of the one or more input controls to rotate one of the one or more instruments may include one or more components that are similar to the rotational movement that is part of a mode switching movement (e.g., where a quick rotation in one direction about an axis is followed by a quick rotation about a similar axis in the opposite direction). As another non-limiting example, a translation of one of the one or more input controls may include one or more components that are similar to the translational movement that is part of a mode switching movement (e.g., where a quick translation in a first direction is followed by a quick translation in approximately an opposite direction). As yet another non-limiting example, when two input controls are being rotated in a "handlebar" mode each of the two input controls may also be rotating about an axis near its respective centroid. According to some embodiments, there are several possible approaches that may be used to determine whether the movement is likely to include one or more components of a mode switching movement depending on whether the mode switching movement includes a rotational component, a translational component, and/or a combination of a rotational component and a translational component. In some examples, the mode switching movement may be different for different modes of operation.

In some embodiments, when the mode switching movement includes a rotational component, the rotational movement of the one or more input controls is further examined. In some examples, the rotational component may include a rotation of one of the one or more input controls about a center point or a coordinated rotation of two input controls about a common center point, such as one located between the two input controls. In some examples, detecting the rotational component of the movement may include tracking the position of each of the one or more input controls over time and fitting the tracked positions to a circular arc to determine a center point of the circular arc, a radius of the circular arc, a rotational axis of the circular arc, an average angular speed around the circular arc, an instantaneous angular speed around the circular arc, and/or the like. In some examples, the fitting may include least-squares fitting. In some examples, the fitting may further include determining whether a maximum and/or an average fitting error is below a configurable threshold before concluding that the movement matches rotation along a circular arc about a center point. In some examples, the configurable threshold may be determined based on one or more of a type of the computer-assisted device, operator preference, a type of the computer-assisted device, a procedure being performed, the current mode of operation, and/or the like. In some examples, the rotational component of the movement may not be detected until the movement includes movement about the circular arc for a configurable period of time. In some examples, the configurable period of time may be 0.2 to 5.0 seconds. In some examples, the configurable period is predetermined and determined prior to disabling mode switching based on mode switching movement. In some examples, the period of time may be set based on one or more of a type of the computer-assisted device, operator preference, a procedure being performed, the current mode of operation, and/or the like. Once the rotational component of the movement is determined to match the circular arc, one or more criteria may be used to determine whether the rotational component of the movement is likely to include one or more components of a mode switching movement.

In some examples, a first criterion may include determining whether a distance (e.g., a Euclidean distance) between the center point of the circular arc is less than a configurable minimum threshold and/or greater than a configurable maximum threshold distance from a centroid of one of the one or more input controls and/or an axis of rotation of one of the one or more input controls. In some examples, the minimum threshold reduces the likelihood of confusing the rotational component for a mode switching movement that includes a rotation about an axis near a centroid of a respective input control. In some examples, the maximum threshold reduces the likelihood of a translational movement being incorrectly characterized as a rotational movement. In some examples, the minimum threshold may be set based on one or more of a size of the one or more input controls (e.g., 1 to 2 cm), a type of the computer-assisted device, operator preference, a procedure being performed, the current mode of operation, and/or the like. In some examples, the maximum threshold may be set based on one or more of a size of the operator console (e.g., 1 to 2 m), a type of the computer-assisted device, operator preference, a procedure being performed, the current mode of operation, and/or the like. In some examples, the maximum threshold may be omitted. In some examples, the distance may be an average distance over a configurable period of time. In some examples, the criterion may include determining whether the distance is less than the minimum threshold and/or greater than the maximum threshold for the configurable period of time. In some examples, the configurable period of time may be 200 ms to 5 seconds. In some examples, the period of time may be set based on one or more of a type of the computer-assisted device, operator preference, a procedure being performed, the current mode of operation, and/or the like. When the distance between the center point and the centroid of one of the one or more input controls is less than the minimum threshold and/or greater than the maximum threshold, the movement is considered to be likely to include one or more components of a mode switching movement.

In some examples, a second criterion may include determining whether an angle between the rotational axis of the circular arc and a rotational axis of the mode switching movement (e.g., an axis of rotation about the centroid of one of the one or more input controls and/or an axis of rotation of one of the one or more input controls) is less than a configurable angular threshold. In some examples, the angular threshold may be 20 to 45 degrees. In some examples, the angular threshold may be set based on one or more of a type of the computer-assisted device, operator preference, a procedure being performed, the current mode of operation, and/or the like. In some examples, vector dot products between the unit axes corresponding to the rotational axes may be used to determine the angle between the rotational axes. In some examples, the angle may be an average angle over a configurable period of time. In some examples, the criterion may include determining whether the angle is less than the angular threshold for the configurable period of time. In some examples, the configurable period of time may be 200 ms to 5 seconds. In some examples, the period of time may be set based on one or more of a type of the computer-assisted device, operator preference, a procedure being performed, the current mode of operation, and/or the like. When the angle between the rotational axes is less than the angular threshold, the movement is considered to be likely to include one or more components of a mode switching movement.

In some examples, a third criterion may include determining whether an angular speed around the circular arc is greater than a configurable angular speed threshold. In some examples, the angular speed threshold may be between 3 and 8 degrees per second. In some examples, the angular speed threshold may be set based on one or more of a type of the computer-assisted device, operator preference, a procedure being performed, the current mode of operation, and/or the like. In some examples, the angular speed may be an average angular speed over a configurable period of time. In some examples, the criterion may include determining whether the angular speed is greater than the angular speed threshold for the configurable period of time. In some examples, the configurable period of time may be 200 ms to 5 seconds. In some examples, the period of time may be set based on one or more of a type of the computer-assisted device, operator preference, a procedure being performed, the current mode of operation, and/or the like. When the angular speed around the circular arc is greater than the angular speed threshold, the movement is considered to be likely to include one or more components of a mode switching movement.

In some examples, a fourth criterion may include determining whether a distance traveled along the circular arc is greater than a configurable distance threshold since entry into the current mode. In some examples, the distance threshold may be between 2 and 5 cm. In some examples, the distance threshold may be set based on one or more of a type of the computer-assisted device, operator preference, a procedure being performed, the current mode of operation, and/or the like. When the distance traveled along the circular arc is greater than the distance threshold, the movement is considered to be likely to include one or more characteristics of a mode switching movement.

In some examples, a fifth criterion may include determining whether force and/or torque applied to the one or more input controls (either each individually and/or in aggregate) against haptic feedback is above a configurable force and/or torque threshold and/or remains above the configurable force and/or torque threshold for a configurable period of time. In some examples, the haptic feedback may be due to a range of motion limit, a collision, a hard locking of one or more of the one or more input control, a soft locking of one or more of the one or more input controls, and/or the like. In some examples, the configurable force threshold may be between 5 and 50 Newtons and/or the configurable torque threshold may be between 0.5 and 50 Newton-meters. In some examples, the period of time may be between 200 ms and 5 seconds. In some examples, the force and/or torque threshold and/or period of time may be set based on one or more of a type of the computer-assisted device, operator preference, a procedure being performed, the current mode of operation, and/or the like. When the force and/or torque against the haptic feedback is above the force and/or torque threshold, the movement is considered to be likely to include one or more components of a mode switching movement.

In some examples, the criterion for whether the rotational component of the movement is likely to include one or more components of a mode switching movement may include a combination of any two, three, four, or all five of the first through fifth criteria. In some examples, the combination may include determining a weighted sum based on how close each of the criteria is to the respective thresholds, a voting technique, and/or the like.

In some embodiments, when the mode switching movement includes a translational component and the movement of at least two input controls are being operated in a coordinated fashion (e.g., in a "handlebar" mode), the translational movement of the at least two input controls is further examined. In some examples, the translational component of the movement of each of the at least two input controls is examined to determine whether each of the at least two input controls is in a same direction and with a same speed. In some examples, two input controls are moving in the same direction when an angle between the directions of each of the two input controls is within a configurable angle of each other. In some examples, the angle may be 45 to 70 degrees. In some examples, the angle may be set based on one or more of a type of the computer-assisted device, operator preference, a procedure being performed, the current mode of operation, and/or the like. In some examples, vector dot products between the unit axes corresponding to the directions may be used to determine the angle between the directions. In some examples, two input controls are moving with a same speed when the speed of the movement of each of the two input controls is within a configurable percentage of each other. In some examples, the configurable percentage is between 15 and 25 percent. In some examples, the configurable percentage may be set based on one or more of a type of the computer-assisted device, operator preference, a procedure being performed, the current mode of operation, and/or the like. In some examples, the translational component of the movement may not be detected until the movement occurs for a configurable period of time. In some examples, the configurable period of time may be 0.2 to 5.0 seconds. In some examples, the period of time may be set based on one or more of a type of the computer-assisted device, operator preference, a procedure being performed, the current mode of operation, and/or the like. Once the translational component of the movement of the at least two or more input controls is determined to have a same direction and a same velocity, one or more criteria may be used to determine whether the translational component of the movement is likely to include one or more components of a mode switching movement.

In some examples, a first criterion may include determining whether an angle between the direction of each of the at least two input controls and the direction of the mode switching movement is less than a configurable angular threshold. In some examples, the angular threshold may be 20 to 40 degrees. In some examples, the angular threshold may be set based on one or more of a type of the computer-assisted device, operator preference, a procedure being performed, the current mode of operation, and/or the like. In some examples, vector dot products between the unit axes corresponding to the directions may be used to determine the angle between the directions. In some examples, the angle may be an average angle over a configurable period of time. In some examples, the criterion may include determining whether the angle is less than the angular threshold for the configurable period of time. In some examples, the configurable period of time may be 200 ms to 5 seconds. In some examples, the period of time may be set based on one or more of a type of the computer-assisted device, operator preference, a procedure being performed, the current mode of operation, and/or the like. When the angle between the direction of each of the at least two input controls and the direction of the mode switching movement is less than the angular threshold, the movement is considered to be likely to include one or more components of a mode switching movement.

In some examples, a second criterion may include determining whether a speed of each of the at least two input controls is above a configurable speed threshold. In some examples, the second criterion may alternately include determining whether an aggregation (e.g., an average) of the speed of each of the at least two input controls is above the configurable speed threshold. In some examples, the speed threshold may be between 2 and 10 cm per second. In some examples, the speed threshold may be set based on one or more of a type of the computer-assisted device, operator preference, a procedure being performed, the current mode of operation, and/or the like. In some examples, the speed may be an average speed over a configurable period of time. In some examples, the criterion may include determining whether the speed is less than the speed threshold for the configurable period of time. In some examples, the configurable period of time may be 200 ms to 5 seconds. In some examples, the period of time may be set based on one or more of a type of the computer-assisted device, operator preference, a procedure being performed, the current mode of operation, and/or the like. When the speed of each of the at least two input controls is above the speed threshold, the movement is considered to be likely to include one or more components of a mode switching movement.

In some examples, a third criterion may include determining whether force and/or torque applied to the at least two input controls (either each individually and/or in aggregate) against haptic feedback is above a configurable force and/or torque threshold. In some examples, the haptic feedback may be due to a range of motion limit, a collision, a hard locking of one or more of the at least two input control, a soft locking of one or more of the at least two input controls, and/or the like. In some examples, the configurable force threshold may be between 5 and 50 Newtons and/or the configurable torque threshold may be between 0.5 and 50 Newton-meters. In some examples, the force and/or torque threshold may be set based on one or more of a type of the computer-assisted device, operator preference, a procedure being performed, the current mode of operation, and/or the like. When the force and/or torque against the haptic feedback is above the force and/or torque threshold, the movement is considered to be likely to include one or more components of a mode switching movement.

In some examples, the criterion for whether the translational component of the movement is likely to include one or more components of a mode switching movement may include a combination of any two and/or all three of the first through third criteria. In some examples, the combination may include determining a weighted sum based on how close each of the criteria is to the respective thresholds, a voting technique, and/or the like.

In some embodiments, when the mode switching movement includes both a translational component and a rotational movement, combinations of any and/or all of the translational and rotational criteria described above may be used to determine whether the movement is considered to be likely to include one or more components of a mode switching movement.

When the movement is considered to be likely to include one or more components of a mode switching movement, mode switching based on mode switching movement is temporarily disabled beginning with a process 430. When the movement is not considered to be likely to include one or more components of a mode switching movement, the movement is examined to determine whether it is a mode switching movement using a process 435.

At the process 430, mode switching based on mode switching movement is disabled. Because the movement of the one or more input controls is likely to include one or more components of a mode switching movement, analysis of the movement to determine whether it is a mode switching movement is temporarily disabled, thus temporarily preventing a mode switch even if the movement is a mode switching movement. In some examples, a configurable timeout period may be started, such as by using a timer. In some examples, the timeout period may be 200 ms to 5 seconds. In some examples, the timeout period may be set based on one or more of a type of the computer-assisted device, operator preference, a procedure being performed, the current mode of operation, and/or the like. Once mode switching based on mode switching movement detection is disabled, method 400 looks for an additional movement of the one or more input controls to occur by returning to process 410.

At the process 435, it is determined whether the movement is a mode switching movement. In some examples, the movement may be examined to determine whether a pattern of tracked position, velocity, acceleration, and/or the like over a period of time (e.g., as captured during process 410) matches a pattern corresponding to a pattern of a mode switching movement. In some examples, the mode switch movement pattern may include a quick rotation of an input control in a first direction about an axis near a centroid of the input control followed by a quick rotation of the input control in a second direction, opposite the first direct, about the same or approximately the same axis. In some examples, the mode switch movement pattern may include a quick movement of the input control in a first direction followed by a quick movement of the input control in a direction approximately opposite the first direction (e.g., up-down, down-up, left-right, right-left, in-out, out-in, and/or the like), a quick zig-zag motion, and/or the like. When the movement is a mode switching movement, the mode is switched using a process 440. When the movement is not a mode switching movement, method 400 looks for an additional movement of the one or more input controls to occur by returning to process 410.

At the process 440, the mode is switched. In some examples, the mode to be switched to is determined by the specific mode switch movement detected during process 435. As a non-limiting example, a quick counter-clockwise rotation of an input control followed by a quick clockwise rotation of the input control may result in switching to a first mode, which is different from a second mode which is switched to when a quick clockwise rotation of the input control is followed by a quick counter-clockwise rotation of the input control. In some examples, the mode switched to may include any of the modes previously discussed including moving an instrument independently from other instruments, moving two or more instruments together, moving an instrument or instruments based on movement of one input control, moving an instrument or instruments based on coordinated movement of two or more input controls, and/or the like. Once in the new mode, method 400 looks for an additional movement of the one or more input controls to occur by returning to process 410.

At the process 445, it is determined whether the temporary disabling of mode switching based on mode switching movement should be ended. In some examples, the temporary disabling should end after a configurable dwell time, such as based on the timeout period started during process 430. In some examples, the temporary disabling should end when the movement is no longer likely to include one or more components of a mode switching movement, such as by using the opposite of any of the criteria and/or combinations of criteria described with respect to process 425. In some examples, the temporary disabling should end when the speed of the movement and/or an average speed of the movement falls below a configurable speed threshold (e.g., 3 to 8 degrees per second for rotational movement and/or 2 to 10 cm per second for translational movement) and/or stays below the configurable speed threshold for a configurable period of time (e.g., 0.5 to 2.0 seconds). In some examples, the temporary disabling should end when force and/or torque applied to the one or more input controls (either each individually and/or in aggregate) against haptic feedback is below a configurable force (e.g., between 5 and 50 Newtons) and/or a configurable torque threshold (e.g., between 0.5 and 50 Newton-meters) and/or remains below the configurable force and/or torque threshold for a configurable period of time (e.g., 200 ms to 5 seconds). In some examples, any of the speed threshold, the force and/or torque threshold, and/or the periods of time may be set based on a type of the computer-assisted device, operator preference, a procedure being performed, the current mode of operation, and/or the like. In some examples, any combination of these criteria (e.g., by weighted sum, voting, and/or the like) may be used to determine whether the temporary disabling should end. When it is determined that the temporary disabling of mode switching based on mode switching movement should end, mode switching based on mode switching movement is enabled using a process 450. When it is determined that the temporary disabling of mode switching based on mode switching movement should continue, method 400 looks for an additional movement of the one or more input controls to occur by returning to process 410.

At the process 450, mode switching based on mode switching movement is enabled. Once mode switching based on mode switching movement is enabled, method 400 looks for an additional movement of the one or more input controls to occur by returning to process 410.

As discussed above and further emphasized here, FIG. 4 is merely an example which should not unduly limit the scope of the claims. One of ordinary skill in the art would recognize many variations, alternatives, and modifications. According to some embodiments, several possible conditions may result in the exiting of method 400. In some examples, method 400 may be exited when the computer-assisted device is placed in a mode where mode switching based on mode switching movement in one or more input controls used to control movement of the one or more instruments is not allowed. In some examples, the switch to a mode where mode switching based on mode switching movement is not allowed may occur as a result of operator action. In some examples, the operator action may include activating and/or deactivating one or more buttons, switches, levers, pedals, dials, and/or the like, activation of one or more GUI elements, a voice command, a hand gesture, as a result of the mode change during process 440, and/or the like. In some examples, other conditions, such as a system fault, disconnection of one or more repositionable arms and/or instruments from an entry guide and/or a cannula, and/or the like may result in the exiting of method 400.

In some embodiments, the processes of method 400 may occur in different orders than those implied by the arrangements of FIG. 4. In some examples, once mode switching based on mode switching movement is enabled during process 450, the movement may be analyzed to determine whether it is a mode switching movement by going to process 435. In some examples, one or more of processes 425 and/or 445 may be performed concurrently with the tracking of process 410 so that the disabling and/or enabling of the detection of mode switching movement occurs as the movement is detected.

Some examples of control units, such as control unit 140 and/or operator console 240 may include non-transitory, tangible, machine readable media that include executable code that when run by one or more processors (e.g., processor 150 and/or processor 243) may cause the one or more processors to perform the processes of method 400. Some common forms of machine readable media that may include the processes of method 400 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and, in a manner, consistent with the scope of the embodiments disclosed herein.

What is claimed is:

1. A computer-assisted device comprising:
an input control;
a repositionable structure; and
a controller coupled to the input control and the repositionable structure;
wherein the controller is configured to:
detect movement of the input control;
control movement of the repositionable structure based on the movement of the input control;
determine whether the movement of the input control is likely to include one or more components of a mode switching movement of the input control, wherein the mode switching movement changes a mode of operation for the computer-assisted device; and
in response to determining that the movement of the input control is likely to include one or more components of the mode switching movement, temporarily disable mode switching in response to movement of the input control.

2. The computer-assisted device of claim 1, wherein:
disabling of mode switching in response to movement of the input control prevents changing of the mode of operation when the movement of the input control is the mode switching movement, and
wherein when mode switching in response to movement of the input control is not disabled, the controller is configured to:
determine whether a second movement of the input control is the mode switching movement; and
in response to determining that the second movement of the input control is the mode switching movement, change the mode of operation of the computer-assisted device.

3. The computer-assisted device of claim 1, wherein the mode of operation is a mode where:
the input control is used to teleoperate an instrument coupled to the repositionable structure; or
coordinated motion of the input control and a second input control is used to teleoperate an instrument coupled to the repositionable structure.

4. The computer-assisted device of claim 1, wherein the mode switching movement includes a first rotational or translational motion of the input control in a first direction followed by a second rotational or translational motion of the input control in a second direction approximately opposite the first direction.

5. The computer-assisted device of claim 1, wherein to determine whether the movement of the input control is likely to include one or more components of the mode switching movement, the controller is configured to:
determine whether the movement of the input control comprises motion along a circular arc, wherein the circular arc has a center point less than a threshold distance from a centroid of the input control or a rotational axis less than a threshold angle from a rotational axis of the mode switching movement.

6. The computer-assisted device of claim 5, wherein to determine whether the movement of the input control is likely to include one or more components of the mode switching movement, the controller is further configured to:
   determine whether the center point of the circular arc is greater than a second threshold distance from the input control.

7. The computer-assisted device of claim 1, wherein to determine whether the movement of the input control is likely to include one or more components of the mode switching movement, the controller is configured to:
   determine whether the movement of the input control comprises motion along a circular arc at an angular speed greater than a threshold speed.

8. The computer-assisted device of claim 1, wherein to determine whether the movement of the input control is likely to include one or more components of the mode switching movement, the controller is configured to:
   determine whether the movement of the input control comprises motion traversing, after the computer-assisted device has entered a current mode of operation, a distance along a circular arc greater than a threshold distance.

9. The computer-assisted device of claim 1, further comprising:
   a second input control;
   wherein to determine whether the movement of the input control is likely to include one or more components of the mode switching movement, the controller is configured to:
      determine whether the movement of the input control and a second movement of the second input control are in a same direction and have a same speed; and
      determine whether an angle between the same direction and a direction of the mode switching movement is less than an angular threshold.

10. The computer-assisted device of claim 1, further comprising:
    a second input control;
    wherein to determine whether the movement of the input control is likely to include one or more components of the mode switching movement, the controller is configured to:
       determine whether the movement of the input control and a second movement of the second input control are in a same direction and have a same speed; and
       determine whether the same speed is greater than a speed threshold.

11. The computer-assisted device of claim 1, wherein to determine whether the movement of the input control is likely to include one or more components of the mode switching movement, the controller is configured to:
    determine whether a force or a torque applied to the input control against haptic feedback is above a threshold.

12. The computer-assisted device of claim 1, wherein to determine whether the movement of the input control is likely to include one or more components of the mode switching movement, the controller is configured to determine whether the movement satisfies two or more criteria, the two or more criteria each being based on at least one parameter selected from a group consisting of: a center point of the movement, a rotational axis of the movement, a speed of the movement, a direction of the movement, and a force or a torque applied to the input control against haptic feedback.

13. The computer-assisted device of claim 1, wherein the temporarily disabling of mode switching in response to movement of the input control occurs until detection of a second movement of the input control that is not likely to include one or more components of the mode switching movement.

14. The computer-assisted device of claim 1, wherein the controller is further configured to enable mode switching in response to movement of the input control in response to detection of a second movement meeting one or more criteria, each of the one or more criteria being based on at least one parameter selected from a group consisting of: a center point of the movement, a rotational axis of the movement, a speed of the movement, a direction of the movement, and a force or a torque applied to the input control against haptic feedback.

15. The computer-assisted device of claim 1, wherein:
    the mode switching movement is one of a plurality of mode switching movements; and
    each mode switching movement of the plurality of mode switching movements changes the mode of operation of the computer-assisted device to a different mode of operation.

16. A method of operating a computer-assisted device, the method comprising:
    detecting, by a controller, movement of an input control of the computer-assisted device;
    controlling, by the controller, movement of a repositionable structure of the computer-assisted device based on the movement of the input control;
    determining, by the controller, whether the movement of the input control is likely to include one or more components of a mode switching movement of the input control, wherein the mode switching movement changes a mode of operation for the computer-assisted device; and
    in response to determining that the movement of the input control is likely to include one or more components of the mode switching movement, temporarily disabling, by the controller, mode switching in response to movement of the input control.

17. The method of claim 16, wherein the mode switching movement includes a first rotational or translational motion of the input control in a first direction followed by a second rotational or translational motion of the input control in a second direction approximately opposite the first direction.

18. The method of claim 16, wherein determining whether the movement of the input control is likely to include one or more components of the mode switching movement comprises:
    determining whether the movement of the input control comprises motion along a circular arc, wherein the circular arc has a center point less than a threshold distance from a centroid of the input control, or greater than a second threshold distance from the input control.

19. The method of claim 16, wherein determining whether the movement of the input control is likely to include one or more components of the mode switching movement comprises:
    determining whether the movement of the input control comprises motion along a circular arc at an angular speed greater than a threshold speed; or
    determining whether the movement of the input control comprises motion traversing, after the computer-assisted device has entered a current mode of operation, a distance along a circular arc for greater than a threshold distance; or determining whether the movement of the input control comprises motion along a circular arc with a rotational axis less than a threshold angle from a rotational axis of the mode switching movement.

20. The method of claim 16, wherein determining whether the movement of the input control is likely to include one or more components of the mode switching movement comprises:

determining whether the movement of the input control and a second movement of a second input control of the computer-assisted device are in a same direction and have a same speed; and determining whether an angle between the same direction and a direction of the mode switching movement is less than an angular threshold or whether the same speed is greater than a speed threshold.

21. The method of claim 16, wherein the temporarily disabling of mode switching in response to movement of the input control occurs until detection of a second movement of the input control that is not likely to include one or more components of the mode switching movement.

22. The method of claim 16, further comprising enabling mode switching in response to movement of the input control in response to detecting of a second movement meeting one or more criteria, each of the one or more criteria being based on at least one parameter selected from a group consisting of: a center point of the movement, a rotational axis of the movement, a speed of the movement, a direction of the movement, and a force or a torque applied to the input control against haptic feedback.

23. A non-transitory machine-readable medium comprising a plurality of machine-readable instructions which when executed by one or more processors of a computer-assisted device are adapted to cause the one or more processors to perform a method comprising:

detecting movement of an input control of the computer-assisted device;

controlling movement of a repositionable structure of the computer-assisted device based on the movement of the input control;

determining whether the movement of the input control is likely to include one or more components of a mode switching movement of the input control, wherein the mode switching movement changes a mode of operation for the computer-assisted device; and in response to determining that the movement of the input control is likely to include one or more components of the mode switching movement, temporarily disabling mode switching in response to movement of the input control.

24. The non-transitory machine-readable medium of claim 23, wherein determining whether the movement of the input control is likely to include one or more components of the mode switching movement comprises:

determining whether the movement of the input control comprises motion along a circular arc, wherein the circular arc has a center point less than a threshold distance from a centroid of the input control, or greater than a second threshold distance from the input control; or determining whether the movement of the input control comprises motion along a circular arc at an angular speed greater than a threshold speed; or determining whether the movement of the input control comprises motion traversing, after the computer-assisted device has entered a current mode of operation, a distance along a circular arc for greater than a threshold distance; or determining whether the movement of the input control comprises motion along a circular arc with a rotational axis less than a threshold angle from a rotational axis of the mode switching movement; or determining whether: the movement of the input control and a second movement of a second input control of the computer-assisted device are in a same direction and have a same speed.

* * * * *